United States Patent [19]
Reiter et al.

[11] Patent Number: 5,391,737
[45] Date of Patent: Feb. 21, 1995

[54] PROCESS FOR THE PREPARATION OF 6,7-DICHLORO-1,5-DIHYDROIMIDAZO[2,1-B]QUINAZOLIN-2[3H]-ONE

[75] Inventors: József Reiter; Péter Trinka; Péter Tömpe; Éva Szabó; Péter Slégel; János Brlik; Ágnes Halbauer née Nagy; Ilona Sztruhár; Magdolna Kenyeres née Fehér; Frigyes Görgényi; Margit Csörgő; Szvetlana Zsarnóczai née Kurnyecova; Sarolta Benkő née Márkus; Gábor Gigler; Dezső Danyi; Pál Fekete; Mária Király née Ignácz, all of Budapest, Hungary

[73] Assignee: EGIS Gyogyszergyar, Budpest, Hungary

[21] Appl. No.: 156,974

[22] Filed: Nov. 24, 1993

Related U.S. Application Data

[63] Continuation-in-part of Ser. No. 886,605, May 21, 1992, abandoned.

[30] Foreign Application Priority Data

May 22, 1991 [HU] Hungary ................ 1707/91
May 22, 1991 [HU] Hungary ................ 1708/91

[51] Int. Cl.$^6$ .......................... C07D 487/04
[52] U.S. Cl. ...................... 544/250; 544/292
[58] Field of Search ............................ 544/250

[56] References Cited

U.S. PATENT DOCUMENTS

| | | | |
|---|---|---|---|
| 3,932,407 | 1/1976 | Beverung, Jr. et al. | 544/250 |
| 3,932,467 | 1/1976 | Miyano | 549/15 |
| 4,146,718 | 3/1979 | Jenks et al. | 544/250 |
| 4,208,521 | 6/1980 | Crenshaw et al. | 544/250 |
| 5,120,845 | 6/1992 | Freyne et al. | 544/250 |

OTHER PUBLICATIONS

Chem. Pharm. Bul. (1980), vol. 28, pp. 1307–1310, Ishikawa et al.

*Primary Examiner*—Emily Bernhardt
*Attorney, Agent, or Firm*—Beveridge, DeGrandi, Weilacher & Young

[57] ABSTRACT

This invention relates to a new and improved process for the preparation of 6,7-dichloro-1,5-dihydroimidazo[2,1-b]-quinazolin-2[3H]-one of formula

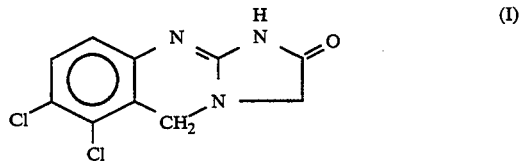

(anagrelide), a valuable blood platelet antiaggregative compound.

According to the process of the invention the compound of formula (I) is prepared by subjecting a new 2-cyanoiminoquinazoline derivative of the general formula

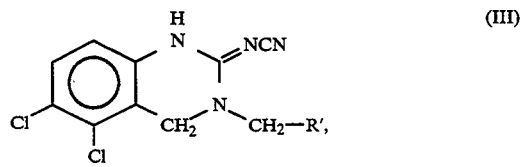

wherein R stands for cyano or a group of the formula COOR$^1$, in the latter R$^1$ representing lower alkyl optionally carrying a phenyl substituent, to thermal cyclization in an acidic medium.

The invention also relates to new 2-cyanoiminoquinazolines of the general formula (III) used for the production of anagrelide and to the preparation of the said compounds.

The invention provides an advantageous process for the preparation of anagrelide which is devoid of the drawbacks of the hitherto known processes and renders possible the production of the compound of the formula (I) on industrial scale, too.

16 Claims, No Drawings

PROCESS FOR THE PREPARATION OF 6,7-DICHLORO-1,5-DIHYDROIMIDAZO[2,1-B]QUINAZOLIN-2[3H]-ONE

This application is a continuation-in-part, of application Ser. No. 07/886,605, filed May 21, 1992, now abandoned, which application is entirely incorporated herein by reference.

This invention relates to a new and improved process for the preparation of 6,7-dichloro-1,5-dihydroimidazo[2,1-b]-quinazolin-2[3H]-one, to new intermediates useful in the preparation of this compound and to a process for the preparation of the said new intermediates.

More particularly, the first subject of the invention is a new and improved process for the preparation of 6,7-dichloro-1,5-dihydroimidazo[2,1-b]quinazolin-2[3H]-one of the formula

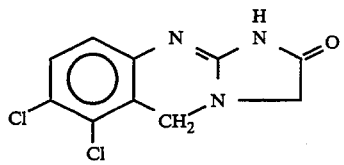
(I)

(referred to further as "anagrelide").

It is known that anagrelide is a valuable blood platelet antiaggregative compound which has been recently reported to be a potent inhibitor of cyclic adenosine monophosphate phosphodiesterase.

Several methods are known for the preparation of anagrelide.

The U.S. Pat. No. 3,932,407 discloses a process for the preparation of anagrelide hydrobromide which comprises boiling a diamine of the general formula

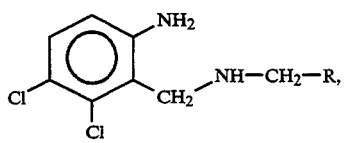
(II)

wherein R is an ester group, with cyanogen bromide in ethanol. The reaction time is rather long, it lasts for 22 hours. An improved method is disclosed in the U.S. Pat. No. 4,146,718. According to this method the diamine of the general formula (II) is boiled with cyanogen chloride, cyanogen bromide or cyanogen iodide for a long time, i.e. for 12 to 18 hours, to yield as intermediate a 2-iminoquinazoline salt of the general formula

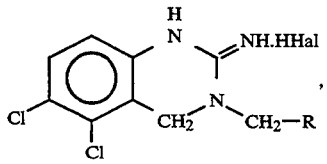
(IV)

wherein R stands for an ester group and Hal represents halogen, and the base liberated from this intermediate is then boiled for 4 hours in ethanol to obtain anagrelide.

A serious drawback of both methods resides in the application of extremely toxic cyanogen halides, requiring special technology and special equipments on an industrial scale production.

According to the process described in the U.S. Pat. No. 3,932,407 a diamine of the general formula (II) is subjected to cyclization with 1,1-carbonyldiimidazole, the corresponding quinazolin-2-one ester of the general formula

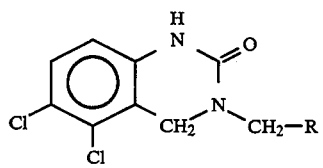
(V)

thus obtained, wherein R is an ester group, is reacted with phosphorus oxychloride to yield the corresponding quinazoline ester of the general formula

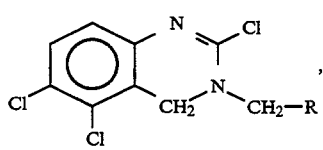
(VI)

wherein R is an ester group, and this latter compound is boiled with ethanolic ammonia to obtain anagrelide. The disadvantages of this process reside in the facts that 1,1-carbonyldiimidazole is a difficultly available substance, and when reacting a quinazolin-2-one ester of the general formula (V) with phosphorus oxychloride, the acid-sensitive ester group decomposes, causing the formation of a considerable amount of by-products. This is the reason why the patent specification discloses only the yield of the crude product and is silent about the losses of purification. The closing step of this synthesis is also disadvantageous since the reaction with ethanolic ammonia is to be carried out at an elevated pressure and the reaction time is rather long, i.e. 16 hours.

The cyclization of a compound of the general formula (VI), wherein R is ethoxycarbonyl, with ethanolic ammonia, is described by Japanese authors. in J. Heterocyclic Chem., 18, 67 (1981), too, but this reaction is also carried out at an elevated pressure in a closed bomb tube, at a temperature of 120° C. for 16 hours, so this process is also disadvantageous for an industrial scale production.

The U.S. Pat. No. 3,932,467 describes a further process for the preparation of the compound of formula (I). According to this process a diamine of the general formula

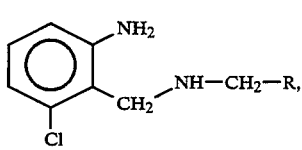
(VIII)

wherein R is an ester group, is reacted with a cyanogen halide to form a quinazolinone of the general formula

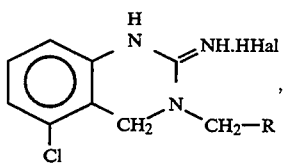
(IX)

wherein R is an ester group, which is then cyclized into an imidazoquinazolinone derivative of the general formula

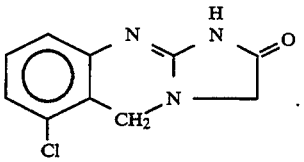
(X)

The latter compound is chlorinated at an elevated pressure, in the presence of anhydrous iron chloride to obtain anagrelide. A serious drawback of this method, in addition to the foregoing ones, resides in the fact that during the chlorination process not only the desired 6,7-dichloro derivative is obtained, but further dichloro isomers, chlorinated in other positions of the aromatic ring, are also formed, and the separation thereof from the compound of formula (I) is rather cumbersome. This may be the reason why the patent specification is silent about the isolation, identification and even the melting point of the compound of the formula (I), only the 6-chloro-7-bromo analogue thereof is described, but yield data are given only for the crude product and neither the losses of purification nor the separation of the isomers are mentioned.

According to the method described in the U.S. Pat. No. 4,208,521 a diamine of the general formula (II), wherein R stands for an ester group, is reacted with a guanile derivative of the general formula

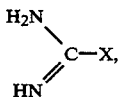
(VII)

wherein X represents a leaving group, to obtain directly anagrelide. As leaving group amino, alkylthio, arylthio and optionally substituted nitrogen-containing heterocyclic groups are mentioned, but only the more reactive 1-guanile-3,5-dimethylpyrazole is specified, which is boiled for as long as 24 hours to obtain anagrelide with a yield of 40%. The very long reaction time and the low yield render this process uneconomical for industrial scale production.

It is the object of the present invention to provide a process which overcomes the drawbacks of the above known methods and enables the favourable preparation of the compound of the formula (I) on industrial scale, too.

According to an aspect of the present invention there is provided a process for the preparation of 6,7-dichloro-1,5-dihydroimidazo[2,1-b]quinazolin-2[3H]-one of the formula (I) and pharmaceutically acceptable salts thereof, which comprises subjecting a 2-cyanoiminoquinazoline derivative of the general formula

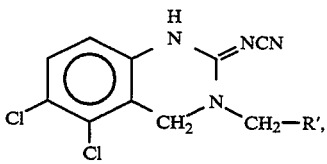
(III)

wherein R' stands for a cyano group or a group of the formula $COOR^1$, in the latter $R^1$ representing a lower alkyl optionally carrying a phenyl substituent, to thermal cyclization in an acidic medium.

In the specification and in the claims the term "lower alkyl" relates to straight or branched alkyl groups having 1 to 6, preferably 1 to 4 carbon atoms such as methyl, ethyl, propyl, isopropyl, butyl, tert-butyl, pentyl, hexyl etc. groups. These groups may be substituted by one phenyl group at any carbon atom.

According to the invention the cyclization is carried out in a mixture of an inert solvent and a mineral acid by boiling for 20 to 180 minutes. Solvents having a boiling point exceeding 80° C. can be used in the reaction, preferably ethylene glycol, diethylene glycol dimethyl ether, diethylene glycol diethyl ether, 2-methoxyethanol, acetonitrile or dioxane. As mineral acid preferably hydrogen chloride is used.

The reaction can also be performed by using as solvent a lower organic acid, preferably acetic acid. In such cases there is not need for using a mineral acid.

The thermal cyclization is preferably carried out at a temperature between 80° C. and 130° C., the reaction is preferably accomplished in 20 to 180 minutes.

When the reaction is accomplished, the reaction mixture is cooled and the product is filtered off either in form of a salt or, after neutralization, in form of a free base.

The starting materials of the general formula (III) are new compounds.

According to a further aspect of the present invention there are provided new 2-cyanoiminoquinazoline derivatives of the general formula (III), wherein R represents a cyano group or a group of the formula $COOR^1$, in the latter $R^1$ stands for lower alkyl optionally carrying a phenyl substituent.

According to a still further aspect of the present invention there is provided a process for the preparation of compounds of the general formula (III), which comprises reacting a diamine of the general formula (II), wherein R represents a cyano group or a group of the formula $COOR^1$, in the latter $R^1$ representing lower alkyl optionally carrying a phenyl substituent, with a cyano derivative of the general formula

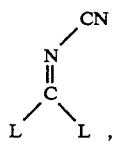
(XI)

wherein L is a leaving group, preferably a group of the formula $XR^2$, in the latter X stands for oxygen or sulfur and $R^2$ is a lower alkyl group optionally carrying a phenyl substituent.

The reaction of the compounds of the general formulae (II) and (XI) is carried out in a solvent inert toward the reactants, preferably in an alcohol or an apolar or polar aprotic solvent. As particularly preferable solvents isopropanol, benzene, dimethylformamide or acetonitrile can be mentioned. The reaction is performed at a temperature between 0° C. and 100° C., preferably between 20° C. and 80° C., particularly preferably at room temperature.

The compounds of the general formula (III) can be isolated from the reaction mixture by methods known per se, generally by conventional filtration followed by recrystallization from an appropriate solvent.

The compounds of the general formula (II) used as starting substances can be prepared e.g. by subjecting the nitro and cyano groups of 2,3-dichloro-6-nitrobenzonitrile to reduction and reacting the compound of formula

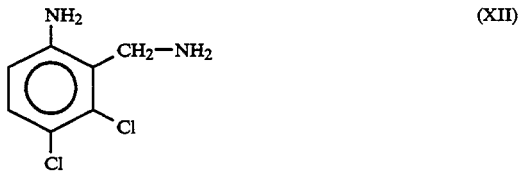
(XII)

thus obtained with a haloacetic acid ester or haloacetic nitrile of the general formula wherein X stands for halogen and R is as stated above.

The invention provides a process for the preparation of anagrelide of formula (I) which is more advantageous than the hitherto known processes due to the elimination of toxic reactants, the simple reaction steps, the short reaction time and the high yield and purity of the product.

Further details of the process are to be found in the following Examples without limiting the scope of protection to the said Examples.

EXAMPLE 1

6,7-Dichloro-1,5-dihydroimidazo[2,1-b]quinazolin-2[3H]-one hydrochloride semihydrate To a solution of 150 ml of ethylene glycol and 15 ml (0.15 moles) of cc. hydrochloric acid 24.5 g (0.075 moles) of ethyl-(2-cyanoimino-5,6-dichloro-1,2,3,4-tetrahydroquinazolin-3-yl) acetate are added in small portions, within about 10 minutes, at 115° C., and the mixture is kept at the same temperature for further 20 minutes. Then it is cooled to room temperature and made neutral by the dropwise addition of 10% potassium carbonate solution. The separated crystals are filtered off. Thus 17.75 g (93.0%) of 6,7-dichloro-1,5-dihydroimidazo[2,1-b]quinazolin-2[3H]-one base are obtained (m.p.>300° C., HPLC content: 99.5%), which is dissolved in a hot mixture of 150 ml of methanol and 150 ml of cc. ethanolic hydrogen chloride (hydrogen chloride content: 0.75 moles/1000 ml). The mixture is then cooled, the separated product is filtered off and washed with a slight amount of ethanol.

Yield: 17.4 (82.8%) M.p.: >300° C., HPLC content: 99.9%.

EXAMPLE 2

6,7-Dichloro-1,5-dihydroimidazo[2,1-b]quinazolin-2[3H]-one hydrochloride semihydrate To a solution of 10 ml of ethylene glycol in 0.5 ml (0.005 moles) of cc. hydrochloric acid, warmed to 120° C., 0.28 g (0.001 mole) of (2-cyanoimino-5,6-dichloro-1,2,3,4-tetrahydroquinazolin-3-yl) acetonitrile are added, and the solution is stirred at the same temperature for 20 minutes. Then it is cooled to room temperature and made neutral with 10% potassium carbonate solution. The separated crystals are filtered off. Thus 0.27 g (96.4%) of crude 6,7-dichloro-1, 5-dihydroimidazo[2,1-b]quinazolin-2[3H]-one base are obtained (m.p.>300° C., HPLC content: 96.3%), which is dissolved in a hot mixture of 7 ml of methanol and 6 ml of cc. ethanolic hydrogen chloride (hydrogen chloride content: 0.76 moles/1000 ml) and allowed to crystallize. Then it is cooled, the separated product is filtered off and washed with a slight amount of ethanol.

Yield: 0.25 g (78.2%) M.p.: >300° C., HPLC content: 99.9%.

EXAMPLE 3

6,7-Dichloro-1,5-dihydroimidazo[2,1-b]quinazolin-2[3H]-one hydrochloride semihydrate To a mixture of 15 ml of ethylene glycol and 2 ml (0.02 moles) of cc. hydrochloric acid, warmed to 120° C., 2.50 g (0.01 mole) of (2-cyanoimino-5,6-dichloro-1,2,3,4-tetrahydroquinazolin-3-yl) acetonitrile are added, and the solution is stirred at the same temperature for 20 minutes. Then it is cooled to room temperature and made neutral with 10% potassium carbonate solution. The separated crystals are filtered off. Thus 2.72 g (97.1%) of crude 6,7-dichloro-1,5dihydroimidazo[2,1-b]quinazolin-2[3H]-one base are obtained (m.p.>300° C., HPLC content: 97.2%), which is dissolved in a hot mixture of 15 ml of methanol and 16 ml of cc. ethanolic hydrogen chloride (hydrogen chloride content: 0.76 moles/1000 ml) and allowed to crystallize. Then it is cooled, the separated product is filtered off and washed with a slight amount of ethanol.

Yield: 2.56 (84.5%) M.p.: >300° C., HPLC content: 99.2%.

EXAMPLE 4

6,7-Dichloro-1,5-dihydroimidazo[2,1-b]quinazolin-2[3H]-one 0.163 g (0.0005 moles) of ethyl (2-cyanoimino-5,6-dichloro-1,2,3,4-tetrahydroquinazolin-3-yl) acetate are added to 2 ml of acetic acid at room temperature, the suspension thus obtained is heated to 100° C. under stirring and kept at the same temperature for 30 minutes. Then it is cooled, the separated crystals are filtered off and washed with acetonitrile.

Yield: 0.116 g (91%) M.p.: >300° C., HPLC content: 99.15%.

EXAMPLE 5

6,7-Dichloro-1,5-dihydroimidazo[2,1-b]quinazolin-2[3H]-one hydrochloride semihydrate 0.2 ml of cc. hydrochloric acid and 0.163 g (0.0005 moles) of ethyl (2-cyanoimino-5,6-dichloro-1,2,3,4-tetrahydroquinazolin-3-yl) acetate are added to 2 ml of diethylene glycol dimethyl ether at room temperature. The reaction mixture is warmed to 110° C. and kept at the same temperature for 60 minutes. The solution is then cooled, the separated crystals are filtered off and washed with ethanol.

Yield: 0.121 g (80%) HPLC content: 86%.

The mother liquor is made alkaline (pH=8) with triethylamine, the free base thus obtained is filtered off and washed with ethanol.

Yield: 0.010 g (7.8%) HPLC content: 90% Total yield: 87.8%.

EXAMPLE 6

6,7-Dichloro-1,5-dihydroimidazo[2,1-b]quinazolin-2[3H]-one hydrochloride semihydrate One proceeds according to Example 5 except that diethylene glycol diethyl ether is used instead of diethylene glycol dimethyl ether.

Yield: 0.123 g (81%) HPLC content: 87.5%.

The yield of the free base obtained form the mother liquor: 0.011 g (8.2%), HPLC content: 91.3%. Total yield: 89.2%.

EXAMPLE 7

6,7-Dichloro-1,5-dihydroimidazo[2,1-b]quinazolin-2[3H]-one hydrochloride semihydrate One proceeds according to Example 5 except that instead of diethylene glycol dimethyl ether ethylene glycol dimethyl ether is used, and the reaction is carried out at 90° C. for 100 minutes.

Yield: 0.124 g (81.8%) HPLC content: 88.2%.

The yield of the free base obtained from the mother liquor: 0.014 g (11%), HPLC content: 93%. Total yield: 92.8%.

EXAMPLE 8

6,7-Dichloro-1,5-dihydroimidazo[2,1-b]quinazolin-2[3H]-one hydrochloride semihydrate One proceeds according to Example 5 except that instead of diethylene glycol dimethyl ether 2-methoxyethanol is used, and the reaction mixture is allowed to crystallize at 0° C. instead of room temperature.

Yield: 0.100 g (66%) HPLC content: 79%.

The yield of the free base obtained from the mother liquor: 0.01 g (7.8%). Total yield: 73.8%.

EXAMPLE 9

6,7-Dichloro-1,5-dihydroimidazo[2,1-b]quinazolin-2[3H]-one hydrochloride semihydrate One proceeds according to Example 8 except that instead of 2-methoxyethanol 2-ethoxyethanol is used, and the reaction mixture is allowed to react for 75 minutes instead of 60 minutes.

Yield: 0.106 g (70%)

The mother liquor is made alkaline with cc. ammonia to obtain 0.013 g (10.3%) of free base. HPLC content: 87.3%. Total yield: 80.3%.

EXAMPLE 12

6,7-Dichloro-1,5-dihydroimidazo[2,1-b]quinazolin-2[3H]-one hydrochloride semihydrate 0.140 g (0.0005 moles) of (2-cyanoimino-5,6-dichloro-1,2,3,4-tetrahydroquinazolin-3-yl)-acetonitrile and 0.2 ml of cc. hydrochloric acid are added to 2 ml of acetonitrile. The reaction mixture is heated to 80° C. under stirring and kept at the same temperature for 50 minutes. Then it is cooled, the separated crystals are filtered and washed with acetonitrile.

Yield: 0.138 g (91.1%), HPLC content: 99.0%.

EXAMPLE 13

6,7-Dichloro-1,5-dihydroimidazo[2,1-b]quinazolin-2[3H]-one

One proceeds according to Example 12 except that instead of acetonitrile dioxane is used, and the reaction mixture is stirred at 100° C. for 30 minutes.

Yield: 0.139 g (91.7%), HPLC content: 99.2%.

EXAMPLE 16

6,7-Dichloro-1,5-dihydroimidazo[2,1-b]quinazolin-2[3H]-one hydrochloride semihydrate 0.140 g (0.0005 moles) of (2-cyanoimino-5,6-dichloro-1,2,3,4-tetrahydroquinazolin-3-yl)-acetonitrile and 0.2 ml of cc. hydrochloric acid are added to 2 ml of 2-methoxyethanol, and the mixture is reacted at 100° C. for 50 minutes. Then it is cooled and allowed to stand overnight in a refrigerator. Then the separated crystals are filtered off and washed with acetonitrile.

Yield: 0.110 g (72.6%), HPLC content: 82%.

The filtrate is made alkaline (pH=8) with cc. ammonia solution, the separated crystals are filtered and washed with water and acetonitrile.

Yield of the free base obtained from the mother liquor: 0.011 g (8.6%), HPLC content: 87.2%.

Total yield: 81.2%.

EXAMPLE 17

6,7-Dichloro-1,5-dihydroimidazo[2,1-b]quinazolin-2[3H]-one hydrochloride semihydrate One proceeds according to Example 16 except that instead of 2-methoxyethanol 2-ethoxyethanol is used.

Yield: 0.115 g (76.0%), HPLC content: 84.5%.

Yield of the free base obtained from the mother liquor: 0.011 g (8.6%), HPLC content: 88.3%.

Total yield: 84.6%.

EXAMPLE 18

6,7-Dichloro-1,5-dihydroimidazo[2,1-b]quinazolin-2[3H]-one hydrochloride semihydrate One proceeds according to Example 16 except that instead of 2-methoxyethanol ethylene glycol dimethyl ether is is used, and the reaction mixture is kept at 90° C. for 70 minutes.

Yield: 0.128 g (84.5%), HPLC content: 92.5%.

Upon adding triethylamine to the mother liquor 0.011 g (8.6%) of 6,7-dichloro-1,5-dihydroimidazo[2,1-b]quinazolin-2[3]H-one base is obtained. HPLC content: 95.7%, total yield: 93.1%

EXAMPLE 19

6,7-Dichloro-1,5-dihydroimidazo[2,1-b]quinazolin-2[3H]-one hydrochloride semihydrate One proceeds as specified in Example 18 except that diethyleneglycol dimethyl ether is used instead of ethylene glycol dimethyl ether.

Yield: 0.127 g (83.8%), HPLC content: 92.3%.

Yield of the free base obtained from the mother liquor: 0.011 g (8.6%), HPLC content: 95.8%.

Total yield: 92.4%.

EXAMPLE 20

6,7-Dichloro-1,5-dihydroimidazo[2,1-b]quinazolin-2[3H]-one hydrochloride semihydrate One proceeds as specified in Example 18 except that instead of 2-methoxyethanol diethylene glycol diethyl ether is used.

Yield: 0.125 g (82.5%), HPLC content: 92.0%.

Yield of the free base obtained from the mother liquor: 0.011 g (8.6%), HPLC content: 94.9%.

Total yield: 91.1%.

EXAMPLE 21

6,7-Dichloro-1,5-dihydroimidazo[2,1-b]quinazolin-2[3H]-one hydrochloride semihydrate 0.140 g (0.0005 moles) of (2-cyanoimino-5,6-dichloro-1,2,3,4-tetrahydroquinazolin-3-yl)-acetonitrile and 0.2 ml of water are added to 2 ml of acetic acid. The reaction mixture is heated to 80° C. under stirring and kept at the same temperature for 30 minutes. Then it is cooled, the separated crystals are filtered and washed with acetonitrile.

Yield: 0.118 g (92.2%) HPLC content: 99.3%.

PREPARATION OF THE STARTING SUBSTANCES

EXAMPLE 22

Ethyl (2-cyanoimino-5,6-dichloro-1,2,3,4-tetrahydroquinazolin-3-yl)acetate

To a suspension of 2.38 g (0.01 mole) of diphenyl-N-cyanoimidocarbonate in 20 ml of acetonitrile a solution of 2.76 g (0.01 mole) of ethyl (2-amino-5,6-dichlorobenzyl)aminoacetate in 20 ml of acetonitrile are added dropwise at 20° to 30° C., within about 30 minutes under stirring. The reaction mixture is stirred further for 1 hour at room temperature, the separated product is filtered off and washed with a slight amount of acetonitrile.

Yield: 1.87 g (57.4%) M.p.: 274°–278° C. (HPLC content: 99.2%).

The mother liquor is treated while hot with charcoal and evaporated to dryness in vacuo. The residue is dissolved in 10 ml of ethyl acetate, the solution is extracted first three times with 50 ml portions of 10% potassium carbonate solution each, then twice with 5 ml of water each, dried, evaporated in vacuo and allowed to crystallize. The separated product is filtered off to yield further 0.66 g (20.2%) of the title compound.

M.p.: 275°–278° C. (HPLC content: 99.5%) Total yield: 77.6%.

EXAMPLE 23

Ethyl (2-cyanoimino-5,6-dichloro-1,2,3,4-tetrahydroquinazolin-3-yl)acetate

To a solution of 0.28 g (0.001 mole) of ethyl (2-amino-5,6-dichlorobenzyl)aminoacetate (GC content: 82%) in 2 ml of benzene 0.24 g (0.001 mole) of diphenyl-N-cyanoimidocarbonate is added at room temperature under stirring, and the reaction mixture is stirred at room temperature for 20 minutes. The separated product is filtered off and washed with a slight amount of benzene.

Yield: 0.21 g (64.4%) M.p.: 263°–270° C. (HPLC content: 98.2%).

The product is recrystallized from 4 ml of dimethylformamide to yield 0.17 g (52%) of pure title compound.

M.p.: 268°–275° C. (HPLC content: 99.9%)

EXAMPLE 24

Ethyl (2-cyanoimino-5,6-dichloro-1,2,3,4-tetrahydroquinazolin-3-yl)acetate

One proceeds as described in Example 23 except that instead of benzene 2 ml of dimethylformamide are used as solvent.

Yield: 0.19 g (58.3%) M.p.: 271°–278° C. (HPLC content: 99.7%).

EXAMPLE 25

Ethyl (2-cyanoimino-5,6-dichloro-1,2,3,4-tetrahydroquinazolin-3-yl)acetate

One proceeds as described in Example 23 except that instead of benzene 2 ml of isopropanol are used as solvent.

Yield: 0.23 g (70.6%) M.p.: 268°–274° C. (HPLC content: 99.5%).

EXAMPLE 26

Ethyl (2-cyanoimino-5,6-dichloro-1,2,3,4-tetrahydroquinazolin-3-yl)acetate

To a solution of 7.68 g (0.023 moles) of ethyl (2-amino-5,6-dichlorobenzyl)aminoacetate (GC content: 82%) in 50 ml of isopropanol 3.8 g (0.0026 moles) of dimethyl-N-cyanoimido this carbonate are added, and the reaction mixture is boiled for 3 hours under stirring. Then it is cooled, the separated product is filtered off and washed with a slight amount of cold isopropanol.

Yield: 2.8 g (37.3%) M.p.: 272°–278° C. (HPLC content: 99.5%).

EXAMPLE 27

(2-Cyanoimino-5,6-dichloro-1,2,3,4-tetrahydroquinazolin-3-yl)acetonitrile

To a suspension of 5.0 g (0.0208 moles) of diphenyl N-cyanoimidocarbonate in 100 ml of acetonitrile 4.61 g (0.02 moles) of (2-amino-5,6-dichlorobenzylamino)acetonitrile are added, the reaction mixture is heated to 60° C. within 20 minutes under stirring and allowed to react at the same temperature for further 1 hour. Then it is cooled, the separated product is filtered off and washed with a slight amount of acetonitrile.

Yield: 3.53 g (60.9%) M.p.: >280° C. (HPLC content: 99.5%).

The filtrate is evaporated to about a third of its original volume to yield 1.2 g (20.7%) of the title compound.

M.p.: >280° C. (HPLC content: 98.7%). Total yield: 81.6%.

EXAMPLE 28

Benzyl (2-cyanoimino-5,6-dichloro-1,2,3,4-tetrahydroquinazolin-3-yl)acetate

To a suspension of 7.2 g (0.030 moles) of diphenyl N-cyanoimidocarbonate in 120 ml of acetonitrile 10.20 g (0.030 moles) of benzyl (2-amino-5,6-dichlorobenzyl)aminoacetate are added, the reaction mixture is heated to 60° C. within 20 minutes under stirring and allowed to react at the same temperature for further 1 hour. Then it is cooled, the separated product is filtered off and washed with a slight amount of acetonitrile and acetone.

Yield: 6.94 g (60.0%) M.p.: 278°–285° C. (HPLC content: 98.9%).

The filtrate is evaporated to about a third of its original volume to yield further 2.0 g (17.3%) of product.

M.p.: 279°–284° C. (HPLC content: 98.4%). Total yield: 77.3%.

EXAMPLE 29

Ethyl (3,4-dihydro-5,6-dichloro-2(1H)-cyanoiminoquinazolin-3-yl)acetate

To a solution of 19.8 g (0.1 M) of dibenzyl (N-cyanoimidodithiocarbonate) in 100 ml of dimethylformamide 27.7 g (0.1 M) of 6-amino-2,3-dichlorobenzylglycine ethyl ester are added, and the reaction mixture is stirred at 100° C. for 5 hours. Then it is cooled, 100 ml of water are added thereto, and it is allowed to crystallize. The separated product is filtered off and washed with a slight amount of isopropanol.

Yield: 10.1 g (31%) M.p.: 274°–277° C.

What we claim is:

1. A process for the preparation of 6,7-dichloro-1,5-dihydroimidazo(2,1-b)quinazolin-2(3H)-one or a pharmaceutically acceptable salt thereof, which comprises subjecting a 2-cyanoiminoquinazoline of the formula

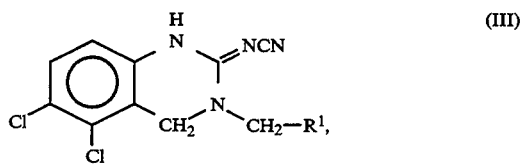

wherein R' stands for cyano or a group of the formula COOR$^1$, in the latter R$^1$ representing lower alkyl optionally carrying a phenyl substituent, to thermal cyclization in an acidic medium, said process further comprising carrying out the reaction in a solvent selected from the group consisting of ethylene glycol, diethylene glycol dimethyl ether, diethylene glycol diethyl ether, 2-methoxyethanol, 2-ethoxyethanol, acetonitrile, dioxane, acetic acid, and ethylene glycol dimethyl ether.

2. A process as claimed in claim 1, which comprises carrying out the reaction in a mixture of said solvent and a mineral acid.

3. A process as claimed in claim 2, which comprises carrying out the reaction at a temperature between 80° C. and 130° C.

4. A process as claimed in claim 2, which comprises using hydrogen chloride.

5. A process as claimed in claim 4, which comprises carrying out the reaction at a temperature between 80° C. and 130° C.

6. A process as claimed in claim 1, which comprises carrying out the reaction at a temperature between 80° C. and 130° C.

7. A process as claimed in claim 1, wherein said process is accomplished in 20 to 180 minutes.

8. A process as claimed in claim 1, wherein said solvent is ethylene glycol.

9. A process as claimed in claim 1, wherein said solvent is diethylene glycol dimethyl ether.

10. A process as claimed in claim 1, wherein said solvent is diethylene glycol diethyl ether.

11. A process as claimed in claim 1, wherein said solvent is 2-methoxyethanol.

12. A process as claimed in claim 1, wherein said solvent is 2-ethoxyethanol.

13. A process as claimed in claim 1, wherein said solvent is acetonitrile.

14. A process as claimed in claim 1, wherein said solvent is dioxane.

15. A process as claimed in claim 1, wherein said solvent is acetic acid.

16. A process as claimed in claim 1, wherein said solvent is ethylene glycol dimethyl ether.

* * * * *